United States Patent
Fournier

(10) Patent No.: US 6,475,165 B1
(45) Date of Patent: *Nov. 5, 2002

(54) CERVICAL SPECIMEN SELF-SAMPLING DEVICE

(75) Inventor: Arthur M. Fournier, Miami, FL (US)

(73) Assignee: Bay Point Group, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/716,648

(22) Filed: Nov. 20, 2000

Related U.S. Application Data

(63) Continuation-in-part of application No. 09/206,760, filed on Dec. 7, 1998, now Pat. No. 6,155,990.

(51) Int. Cl.$^7$ ............................................. A61B 10/00
(52) U.S. Cl. ........................ 600/572; 600/562; 600/573
(58) Field of Search ................................ 600/562, 569, 600/572, 573; 604/1, 2, 11, 15, 18, 317, 328, 330, 358, 904; 606/160

(56) References Cited

U.S. PATENT DOCUMENTS

| | | | |
|---|---|---|---|
| 2,847,000 A | | 8/1958 | Nieburgs |
| 3,776,219 A | | 12/1973 | Brown |
| 3,800,781 A | * | 4/1974 | Zalucki ..................... 600/562 |
| 3,857,384 A | | 12/1974 | Watson |
| 3,995,618 A | | 12/1976 | Kingsley et al. |
| 4,157,709 A | * | 6/1979 | Schuster et al. ............. 600/572 |
| 4,754,764 A | * | 7/1988 | Bayne ......................... 600/569 |
| 4,945,921 A | | 8/1990 | Okimoto |
| 4,952,204 A | | 8/1990 | Korteweg |
| 5,121,752 A | | 6/1992 | Canna |
| 5,339,828 A | | 8/1994 | Keating et al. |
| 5,445,164 A | * | 8/1995 | Worthen et al. ............. 600/572 |
| 5,795,309 A | * | 8/1998 | Leet et al. ................... 600/569 |
| 5,830,154 A | | 11/1998 | Goldstein et al. |
| 6,036,658 A | * | 3/2000 | Leet et al. ................... 600/569 |
| 6,155,990 A | * | 12/2000 | Fournier ...................... 600/572 |

* cited by examiner

*Primary Examiner*—Max Hindenburg
*Assistant Examiner*—Charles Marmor, II
(74) *Attorney, Agent, or Firm*—Malloy & Malloy, P.A.

(57) ABSTRACT

A human female cervical specimen gathering device is disclosed which can be self administered by women. This device is an improvement over conventional cervical tissue sampling, which requires a speculum examination, and prior self-sampling devices, which are not compatible with thin-prep cytology easily adaptable to existing pap-smear technology, for thin smear cytology (automated or manual) microbial cultures and assays such as polymer-chain-reaction assays for human papilloma virus. The device consists of a cardboard tube that houses a retractable sponge. The handle is adapted to allow it to serve as a screw-cap lid, once the device is inserted into a conical tube containing fixative or preservative. After transport to the lab the tube can easily be agitated to liberate cells, centrifuged, and prepared as a thin smear for cytology or DNA probes.

11 Claims, 2 Drawing Sheets

CERVICAL SPECIMEN SELF-SAMPLING DEVICE

CLAIM OF PRIORITY

The present application is a continuation-in-part application of previously filed, co-pending application having Ser. No. 09/206,760, filed on Dec. 7, 1998, which matured into U.S. Pat. No. 6,155,990.

BACKGROUND OF THE INVENTION

1. Field of the Invention

Screening for cervical cancer in women using cytological techniques has been possible for more than 40 years. The papanicolau test (pap test) has allowed for a significant reduction in mortality in women from cervical cancer. Prior to the pap test, cervical cancer was the most common cause of cancer deaths in women. In countries where pap smears are available, mortality from cervical cancer is negligible.

2. Description of the Related Art

In spite of this progress, there are several problems with the present technology. Conventional pap tests show a high percentage of smears of undetermined significance that requires further testing. This problem has led to the development of "thin prep" technology. Thin prep technology requires that cells be immersed in fixative and centrifuged prior to analysis. Other advances in diagnostic technology are the discovery of DNA probes for human papilloma virus (HPV), the causative agent of cervical cancer, and for chlamydia, a common infection in women. Tests for HPV may soon replace conventional pap smears as the initial screening test for cervical cancer. Collection of cytologic specimens currently requires a speculum examination which is frequently uncomfortable and embarrassing for women. It is also relatively expensive, since it requires the services of a physician or nurse practitioner. Finally, the specimen obtained is applied directly to a glass slide, which is not compatible with automated cytologic analysis or necessary for HPV assay. The same problems of discomfort, embarrassment, expense and processing also apply to the obtaining of specimens to diagnose vaginal infections such as candidiasis, gonorrhea, human papilloma virus and chlamydia.

Prior self sampling devices (described in the next section) were either designed prior to the invention of thin prep and HPV assay technologies or designed specifically to obtain a specimen in the setting of a conventional speculum examination. Given these problems, there is a need for an improved, inexpensive self sampling device which asymptomatic women can use in the privacy of their home that is adaptable to automated cytology methods (thin smear), HPV assay and microbial culture. This application discloses just such an improvement.

Several previously disclosed self sampling devices have failed because they fail to protect the sample from vaginal secretions and contamination (ex. U.S. Pat. Nos. 2,847,000; 3,776,219; 3,857,384). Below are described previously disclosed devices that are designed to protect the sample from vaginal contamination:

U.S. Pat. No. 5,121,752 discloses a self sampling device that utilizes a relatively large diameter hollow cylindrical speculum coupled with a mirror-guided hinged spatula. This device is not applicable for mass screening, since it is uncomfortable for many women to insert, and technically difficult for most women to manipulate in order to obtain an adequate specimen (to do this at home, it would require the manipulation of the speculum, the spatula, a mirror and a light source).

U.S. Pat. No. 3,995,618 discloses a double barreled plastic tube with a sponge on one end for self-sampling of cervical tissues. This device has some beneficial features including its simplicity of use and ability to protect the specimen from vaginal contamination. However, its plastic construction increases its expense and it is unnecessarily complicated, with an unwinding sponge which is dragged across an internal slide to: obtain the specimen. It is also not biodegradable and is more difficult to utilize than that of this disclosure. The device is therefore not designed to be inserted into a conical tube after the specimen is obtained, with the handle serving as the screw-cap seal - a feature which will allow the present proposed device to adapt to thin smear cytologic technique and microbiologic culture and HPV assay. It should be noted that thin smear cytology, automated cytology and microbiologic assays such as polymerase chain reaction or PCR tests did not exist when U.S. Pat. No. 3,995,618 was disclosed.

U.S. Pat. No. 2,847,000 is the prototype cervical self sampling device (filing date, Jul. 2, 1997). This device is designed to obtain cervical cytology specimens through a tampon-like device and then transfer the specimen to a slide enclosed within the tampon. This device never was put to clinical use. Its design is flawed because the cervical cells will adhere to the anterior portion of the sponge in a position that will not be transferable to the slide. This device is not compatible with thin prep technology.

U.S. Pat. No. 5,830,154 discloses a cylindrical tube with a slide attached to a screw cap allowing it to be immersed in fixative. It is not a self sampling device, although it could be modified slightly to be the receptacle of specimens obtained by this invention.

U.S. Pat. No. 4,945,921 discloses a vaginal self-sampling device designed exclusively to test vaginal pH. It cannot be used for cytologic or microbiological assay.

U.S. Pat. No. 4,952,204 discloses a swab with a handle enclosed in a sheath to protect the swab from contamination. The device was not designed for cervical self-sampling, nor is such an intent claimed—the purpose of the device is simply to maintain the sterility of the swab.

U.S. Pat. No. 5,339,828 discloses a device for obtaining specimens by trained clinicians through endoscopy. It is not practical or compatible with cervical self sampling.

U.S. Pat. No. 5,445,164, Worth et al. described an alternative approach to cervical self sampling, and is rather elaborate in design. Although this design seeks to address many of the issues and problems of self sampling, it is designed to be mailed in after use, as opposed to being immediately immersed in a fixative or preservative. This, at a minimum creates extra steps in handling and may interfere with the technique, sensitive and specificity of thin prep cytology. Again, it should be noted that this device was invented prior to the FDA approval of thin prep cytology (1996).

U.S. Pat. No. 3,857,384 is a cervical self sampling device in which specimens are sampled directly onto a smear. It is thus not compatible with thin prep cytology.

U.S. Pat. No. 4,164,212 discloses a device for obtaining mucus to determine menstrual phase. This is a device designed to evaluate problems with fertility, not cervical cancer or vaginal infections.

SUMMARY OF THE INVENTION

Accordingly, the present invention comprises a tampon-like device that will allow for the self sampling of cervical specimens. As such, the cervical sampling device comprises a tampon-like tube preferably made of a medical grade cardboard material, wherein the cardboard tube is structured to move or be selectively telescoped between an extended orientation and a compressed orientation. An extrudable and retractable sponge is housed within the cardboard tube and is sized for entry into the vaginal cavity so as to painlessly obtain cervical specimens utilizing a self-sampling procedure. Also, a handle is attached to the sponge and may form a screw cap of the type which is structured to be secured to a standard tube in which a fixative is contained such that the obtained sample is adequately preserved. The extended orientation of the tube serves to position the sponge on the interior thereof and the aforementioned compressed orientation selectively disposes the sponge or collection element outwardly from the tube to facilitate collection of the cervical specimen. The device will be inexpensive to produce, easy to destroy after use, and easy for women to use. It will allow for the safe transportation of the specimens to laboratories for analysis and is easily adaptable for centrifugation and thin-film preparation, or DNA probe for HPV, which is a technological improvement over the older direct preparation for a smear.

In a more limited application of this device, it can also be used to obtain specimens for culture or microbiologic assay. This will make it useful in the diagnosis of vaginal infections and for epidemiologic studies of sexually transmitted diseases.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
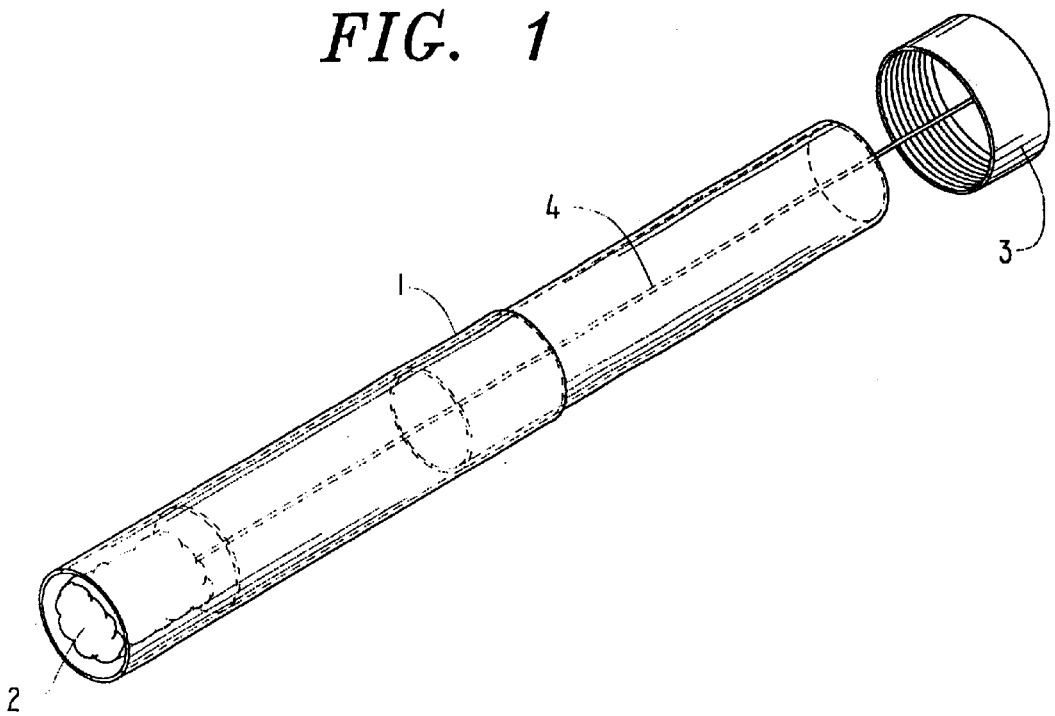
FIG. 1 is a perspective view of the self sampling device, taken from one side and below.
Figure 2:
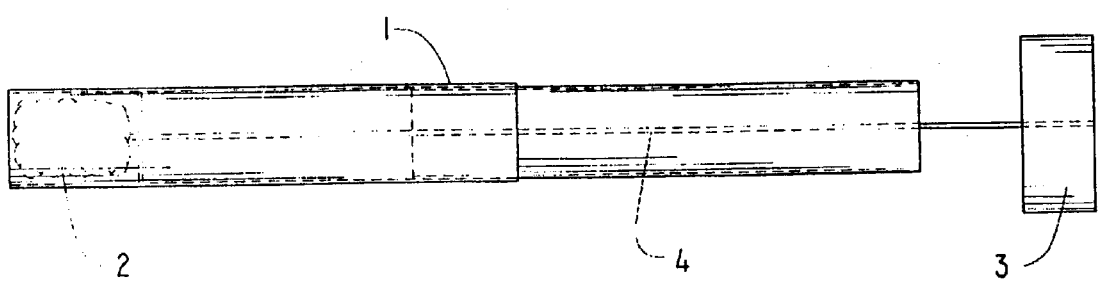
FIG. 2 is a cross-sectional view demonstrating the internal design.
Figure 3:
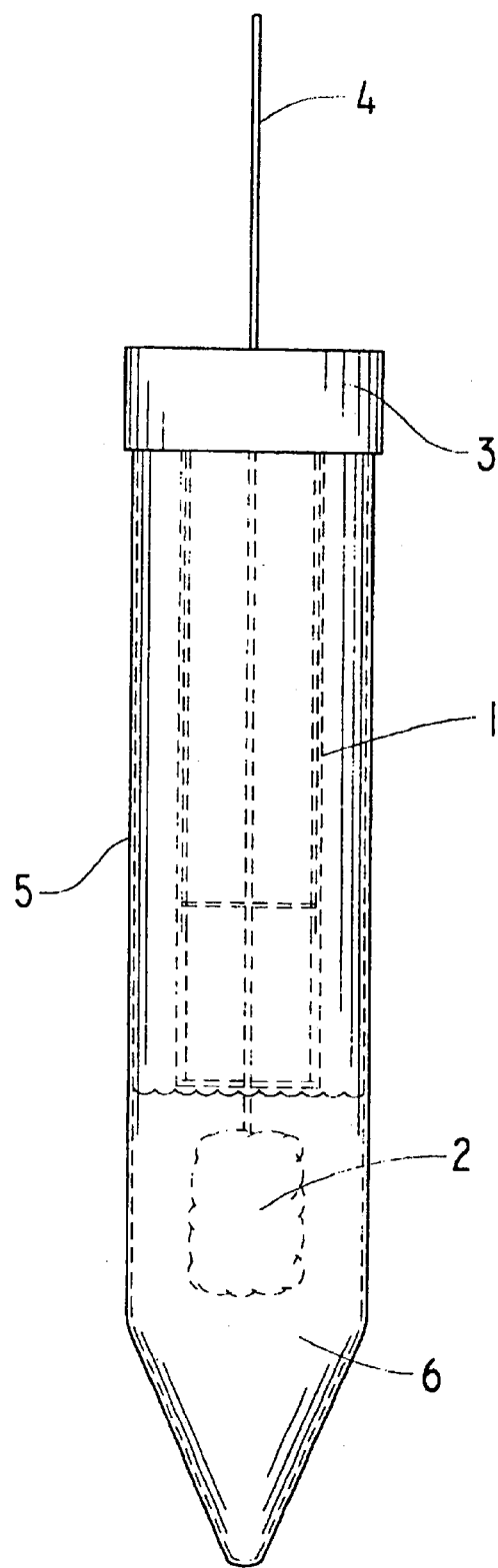
FIG. 3 is a diagram demonstrating how the device is designed to fit and seal a standard cylindrical tube, in order to process the specimen using thin-film cytology.

Please refer to FIGS. 1–3 for a complete understanding of this invention. The drawings represent the current best conceptualization of the design, and are not to be construed as a restriction or limitation of the scope of the present invention.

As can be seen in FIGS. 1 and 2, the device is an assembled unit consisting of the subunits: a) a tube, such as a "telescoping" cylindrical tampon-like cardboard sheath (1) which houses b) the specimen-gathering collection element, such as a is sponge (2). The sponge is attached to the c) screw-cap handle (3) by an elongate segment such as a square dowel (4) that perforates a rubber seal in the handle.

The cylindrical tampon sheath (1) is constructed of medical-quality cardboard and coated with wax or Teflon to allow for minimal friction on insertion. With the "telescope" fully extended and the sponge housed in the anterior chamber of the sheath (1), the device is inserted into the vaginal cavity until resistance is met. By grasping the posterior end of the sheath (1) between the first two fingers and pressing on the handle (3) with the thumb, the sponge (2) will extend into the vaginal vault.

The sponge may be composed of several possible flexible, perhaps resilient materials, including, but not limited to cellulose, natural or artificial sponge material. The sponge may have good adherent and mildly abrasive qualities. The vacuum created by the sponge upon insertion should draw cells down from the cervical canal without the trauma that might be created by a traditional spatula. It also obviates the need for direct visualization of the cervical os.

After insertion of the sheath and extrusion of the sponge, the handle (3) is rotated to obtain the specimen and then retracted in order to return the sponge to the anterior chamber prior to removal. A rim on the inner tube and a groove on the inner surface of the outer tube will assure that the telescope mechanism does not collapse prior to the sponge returning to the anterior chamber.

The overall length of the device is 15 cm. The length of the sheath will be 13 cm when fully extended and disposed in an extended orientation. The maximum width will be 1.5 cm. These dimensions will accommodate the standard vaginal depth of 12.7 cm for a mature woman, and are sufficiently narrow to allow for comfortable insertion. The device will collapse to 7 cm, so as to define a compressed orientation, allowing it to be easily inserted into a standard conical tube (5) of 11.5 cm in depth. The screw-cap handle is designed so that the cap will form a tight seal on the conical tube (5). The dowel (4) will extend above the handle (see FIG. 3), its length of protrusion fixed by the collapse of the telescope and the need for the sponge to be freely immersed in the fixative (6).

The sponge will be immediately immersed in the fixative after removal of the device from the patient, avoiding problems associated with drying. Upon arrival at the laboratory, the device-fixative-tube will be agitated to liberate cells from the sponge, centrifuged and the supernatant discarded. The cellular contents will be removed and prepared as a thin-film slide for either manual or automated cytologic examination using conventional cytologic techniques. The device can then be disposed of using "universal precautions" and incinerated.

By simply changing the solution in the conical tube, the device can easily be adapted for culture, "wet mount", KOH prep for fungal examinations or PCR assays for chlamydia and human papilloma virus. Although the device is primarily designed for self-sampling of cytologic specimens, it may have wide applications in the diagnosis of vaginal infections, in conducting epidemiologic studies of sexually transmitted diseases or in comparing the utility of PCR assay for human papilloma virus to conventional cytology as a screening test for cervical cancer. While several embodiments of the inventive concept have been described, it is understood that the invention is not to be construed as limited thereby, and that suitable modifications and variations may be made without departing from the spirit and scope of the invention as described in the following claims.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. A cervical self-sampling device for the self-sampling of culture material or specimens for use in thin smear cytology techniques, microbiologic assay, and epidemiologic studies, said device comprising:

a tampon-like telescoping cardboard tube;

an extrudable and retractable sponge housed within said telescoping cardboard tube, said sponge sized for the painless self-sampling of cervical specimens;

a handle attached to said sponge, the handle forming a screw cap for a standard tube for sealing and preserving a sample in a fixative contained within the standard tube, and said tube being structured to telescope between an extended orientation, wherein said sponge is contained within said tube, and a compressed orientation wherein said sponge extends from said tube so as to collect the cervical specimen.

2. A cervical self-sampling device comprising:

a tube structured to be at least partially introduced into a vaginal cavity of a patient;

a collection element at least temporarily housed within said tube, said collection element structured to engage a patient within the vaginal cavity and collect a cervical specimen therefrom;

a handle attached to said collection element, said handle defining a cap structured to engage a specimen tube for sealing and preserving the cervical sample in a fixative contained within the specimen tube, and said tube being structured to telescope between an extended orientation wherein said collection element is contained within said tube, and a compressed orientation wherein said collection element extends from said tube so as to collect the cervical specimen.

3. The cervical self-sampling device recited in claim 2 further comprising an elongate segment disposed between said cap and said collection element so as to remotely extend said collection element into a sample collecting position within the vaginal cavity.

4. The cervical self-sampling device recited in claim 2 wherein said collection element includes a flexible material configuration structured to accommodate the sample thereon.

5. The cervical self-sampling device recited in claim 4 wherein said collection element includes an at least partially abrasive surface structured to at least partially collect the sample upon engaging the patient.

6. The cervical self-sampling device recited in claim 4 wherein said collection element includes an at least partially resilient configuration structured to contact the patient and draw the cervical specimen thereon.

7. The cervical self-sampling device recited in claim 6 wherein said collection element is structured to generate a vacuum within the vaginal cavity upon partial withdrawal thereof from said contact with the patient, so as to draw the cervical sample towards said collection element.

8. The cervical self-sampling device recited in claim 5 wherein said collection element includes a sponge.

9. The cervical self-sampling device recited in claim 2 wherein said collection element is structured to be contained within said tube upon said tube being introduced into the cervical cavity.

10. The cervical self-sampling device recited in claim 9 wherein said handle is structured to urge said collection element from said tube and into said engagement with the patient at least when said tube extends into the cervical cavity of the patient.

11. The cervical self-sampling device recited in claim 2 wherein said cap defined by said handle includes a threaded configuration structured to matingly engage cooperating structure on the specimen tube.

* * * * *